United States Patent [19]

Ross et al.

[11] 4,417,080

[45] Nov. 22, 1983

[54] SOLVENT MODIFICATION OF NITRATIONS BY $N_2O_4$/METAL ACETYLACETONATE SYSTEMS

[75] Inventors: David S. Ross, Palo Alto; Robert M. Johnson, Jr., San Mateo; Ripudaman Malhotra, Menlo Park, all of Calif.

[73] Assignee: Air Products and Chemicals, Inc., Allentown, Pa.

[21] Appl. No.: 386,857

[22] Filed: Jun. 10, 1982

[51] Int. Cl.$^3$ .............................................. C07C 79/10
[52] U.S. Cl. .................................................. 568/939
[58] Field of Search ............... 568/927, 928, 929, 930, 568/931, 932, 939, 940

[56] References Cited

U.S. PATENT DOCUMENTS

| | | | |
|---|---|---|---|
| 1,325,168 | 12/1919 | Perruche . | |
| 2,109,873 | 3/1938 | Wilhelm | 260/142 |
| 2,431,585 | 11/1947 | Rout | 260/645 |
| 3,459,816 | 8/1969 | Pritchett | 260/645 |
| 3,856,859 | 12/1974 | Moore et ,l. | 260/556 |
| 3,922,315 | 12/1975 | Mitchell, Jr. et al. | 260/645 |
| 3,929,916 | 12/1975 | Levy et al. | 568/940 |
| 3,929,917 | 12/1975 | Rauch et al. | 260/645 |
| 4,028,425 | 6/1977 | Gilbert | 260/645 |
| 4,104,145 | 8/1978 | Ando | 204/162 |
| 4,123,466 | 10/1978 | Lin et al. | 260/645 |

OTHER PUBLICATIONS

D. S. Ross and W. G. Blucher, "A Novel Nitration System" 174th Meeting of Am. Chem. Soc., Chicago, Ill., Aug. 1977.

*Primary Examiner*—Leland A. Sebastian
*Attorney, Agent, or Firm*—Michael Leach; E. Eugene Innis; James C. Simmons

[57] ABSTRACT

Aromatic hydrocarbons are nitrated by reacting the aromatic hydrocarbon in a nitrogen tetroxide-containing liquid reaction medium, in the presence of a beta-dicarbonyl compound having a "W" configuration with a carbonyl group at each apex of the "W", such as a metal acetylacetonate, preferably at a pressure and temperature sufficient to maintain the nitrogen tetroxide in the liquid state. Addition of an inert organic co-solvent to the liquid nitrogen tetroxide for the metal acetylacetonate promoted nitration of benzene essentially eliminates the production of dinitrobenzenes.

16 Claims, No Drawings

4,417,080

SOLVENT MODIFICATION OF NITRATIONS BY N₂O₄/METAL ACETYLACETONATE SYSTEMS

CROSS-REFERENCE TO RELATED APPLICATIONS

This application is related to our co-filed application titled "Beta-Dicarbonyl Compounds For The Promotion Of Aromatic Nitration By Nitrogen Tetroxide," Ser. No. 386,856, which is incorporated by reference.

TECHNICAL FIELD

This invention relates to a process for the nitration of aromatic hydrocarbons. More particularly, this invention is concerned with an improved process for the selective nitration of benzene by nitrogen tetroxide.

BACKGROUND OF THE INVENTION

The nitration of aromatic hydrocarbons, and, in particular, of benzene and toluene, is normally carried out on a commercial scale by reacting the aromatic hydrocarbon with a mixture of nitric and sulfuric acids under controlled temperature. This mixed acid process suffers from the use of large volumes of the highly corrosive mixture of nitric and sulfuric acids and the formation of by-products including the highly undesirable and potentially explosive polynitrated hydrocarbons.

Various methods for nitrating aromatic hydrocarbons without the use of a mixed acid are known:

U.S. Pat. No. 1,325,168 describes passing an oxidizing agent, such as oxygen, into a mixture of an aromatic hydrocarbon and liquid nitrogen peroxide.

U.S. Pat. No. 2,109,873 describes passing a gaseous mixture of an aromatic hydrocarbon and nitrogen dioxide through a bed of silica gel to obtain the mononitro derivative of the aromatic hydrocarbon.

U.S. Pat. No. 2,431,585 describes the vapor phase nitration of an aromatic hydrocarbon to produce the mononitro derivative using nitrogen dioxide and a catalyst which is selected from metal metaphosphate, boron phosphate, solid and supported phosphoric acid.

U.S. Pat. No. 3,459,816 describes nitrating a dialkylbenzene with dinitrogen tetroxide in a halogenated hydrocarbon solvent at a temperature of about 90° to 160° C. to effect substitution of the nitro group on the alkyl substituent.

U.S. Pat. No. 3,856,859 discloses the position-selective nitration of alkanesulfonanilides using an equimolar amount of a nitrating agent, such as dinitrogen tetroxide in chloroform or trifluoroacetic acid.

U.S. Pat. No. 3,922,315 describes a process for the mononitration of aromatic compounds by contacting the aromatic compound with nitrogen dioxide and/or its dimer, nitrogen tetroxide, in the presence of a rhodium catalyst and hydrogen.

U.S. Pat. No. 3,929,917 discloses a process for mononitrating ortho-xylene by reacting the ortho-xylene with nitrogen tetroxide (N₂O₄) or nitrogen dioxide (NO₂) and an oxygen containing gas in the presence of a mercuric salt dissolved in acetic acid at temperatures above about 20° C.

U.S. Pat. No. 4,028,425 describes a continuous process for the concurrent production of dinitrotoluene and nitric acid by continuously introducing toluene, nitrogen dioxide or nitrogen tetroxide and oxygen in specified molar ratios into a reaction zone containing a reaction medium comprising dinitrotoluene and 93–103% nitric acid.

U.S. Pat. No. 4,104,145 describes the nitration of benzene by the use of nitrogen dioxide under irradiation of visible ray or ultra violet ray in the presence of oxygen.

U.S. Pat. No. 4,123,466 describes reacting an aromatic hydrocarbon with gaseous nitrogen dioxide in the presence of a catalytic amount of sulfuric acid and in the absence of oxygen.

D. S. Ross and W. G. Blucher, "A Novel Nitration System," 174th meeting of Am. Chem. Soc., Chicago, Ill., August 1977, disclosed the production of nitrobenzenes by dissolving benzene and nitric oxide (NO) in liquid $N_2O_4$ at 0° C. under 2 atmospheres oxygen.

SUMMARY OF THE INVENTION

In its broadest aspect, the invention comprises reacting benzene with nitrogen tetroxide ($N_2O_4$) in an inert organic solvent containing an effective amount of a metal acetylacetonate at a temperature sufficient to effect nitration, preferably under a pressure which is sufficient to maintain the nitrogen tetroxide in the liquid state at the reaction temperature.

The use of an inert organic solvent with the nitrogen tetroxide as the nitration reaction medium for benzene affords the selective production of mononitro-substituted benzene.

Compared to prior art liquid $N_2O_4$ reactions, an additional advantage of this invention for mononitrating benzene is the substantial suppression of phenolic by-product formation. A further advantage is the elimination of the use of an acidic material, such as aqueous sulfuric acid, acetic acid, trifluoroacetic acid and the like, in the nitration reaction medium.

DETAILED DESCRIPTION OF THE INVENTION

The invention relates to a process for the nitration of an aromatic hydrocarbon and comprises reacting benzene with $N_2O_4$ in an inert organic solvent containing an effective amount of a metal acetylacetonate at a temperature sufficient to effect reaction between the benzene and the $N_2O_4$, and preferably under a pressure sufficient to maintain the $N_2O_4$ essentially as a liquid at the reaction temperature.

The nitrogen tetroxide component of the liquid nitration reaction medium may be liquid nitrogen tetroxide which is an equilibrium mixture of $NO_2$ and $N_2O_4$ having a melting point of about −11° C. and a boiling point of about 21° C. at atmospheric pressure. Although only a limited amount of $N_2O_4$ is required for each mole of aromatic hydrocarbon to afford the mononitro derivative, liquid $N_2O_4$ is advantageously used in considerable excess.

It has unexpectedly been discovered that a liquid nitrogen tetroxide/inert organic solvent reaction medium containing a metal acetylacetonate substantially eliminates the formation of dinitrosubstituted benzenes. By an "inert organic solvent" is meant a liquid organic compound which does not substantially react with the $N_2O_4$, metal acetylacetonate or co-products under the conditions of the nitration reaction.

Contemplated as the functional, or operative, equivalent of a liquid $N_2O_4$/inert organic solvent reaction medium for purposes of the invention is the inert organic solvent containing dissolved gaseous nitrogen tetroxide, especially such solvent saturated with gaseous nitrogen tetroxide.

Representative inert organic solvents which can be used as solvents in the process of this invention for the selective production of mononitrated benzene include, for example, nitroaliphatics and nitroaromatics, acyclic and cyclic aliphatics, and halogenated aliphatics. Specific examples of such solvents are nitromethane, nitroethane, nitrobenzene, cyclohexane, methylene chloride, chloroform, carbon tetrachloride, trichlorotrifluoroethane, and the like.

The amount of inert organic solvent used in the practice of the invention with respect to the amount of nitrogen tetroxide, benzene or metal acetylacetonate is not critical although it is preferred to use excess quantities, e.g. a volume of solvent about equal to or greater than the volume of liquid nitrogen tetroxide.

Advantageously, the metal acetylacetonate compound for practicing the process described herein should be soluble in the reaction medium. "Soluble" means that the compound is capable of sufficiently dissolving in the liquid reaction medium to yield a solution that is effective for practicing the inventive process. Needless to say, the more soluble the metal acetylacetonate compound in the nitration reaction medium the better.

The compounds useful as promoters for the mononitration of benzene using nitrogen tetroxide are the metal salts of acetylacetone (2,4-pentanedione) which has an active hydrogen atom attached to the methylene carbon atom.

The metal acetylacetonate compounds are prepared by reacting acetylacetone having such active hydrogen atom with, for example, an oxide, hydroxide, carbonate, hydride or the like of a metal such as an alkali, alkaline earth or transition metal in an appropriate solvent as is well known in the art. Exemplary of suitable metal acetylacetonates are cobalt(III)acetylacetonate, iron(III)acetylacetonate, lithium acetylacetonate, copper(II)acetylacetonate, manganese(III)acetylacetonate, cerium(IV)acetylacetonate, potassium acetylacetonate, magnesium acetylacetonate and the like.

The preferred metal acetylacetonate compounds are those compounds in which the metal is a transition metal, particularly the first row transition metals of the Periodic Table, and especially those transition metals having available oxidation states separated by one unit. However, transition metals with oxidation states separated by two or more units may be used in the invention. For example, acetylacetonates of titanium, vanadium, chromium, manganese, iron, cobalt, nickel or copper may be used.

Metal acetylacetonates may be identified as $M(acac)_n$ where M represents a metal ion, n is the oxidation number of the metal ion and (acac) represents the acetylacetonate radical.

The above-mentioned metal acetylacetonate compounds are not intended to be exhaustive of those which may be employed in the reaction. However, as might be expected, it is preferred to use those which are more reactive and provide for substantial conversion with high selectivity to the desired mononitrosubstituted product.

The quantity of soluble metal acetylacetonate used in the nitration reaction is empirical and can vary widely depending upon the reactivity of the metal acetylacetonate compound and the reactivity of the benzene. An effective amount of a soluble metal acetylacetonate compound is used; in other words, an amount which causes a reaction between the benzene and the nitrogen tetroxide to yield mononitrobenzene at the temperature and pressure used. Usually, though, the amount used ranges from about 5 to 40 mole % or more based upon the total amount of the benzene present in the reaction mixture, and preferably in an amount from about 5 to 10 mole %. When the nitration promoter is a transition metal acetylacetonate, it may be used in an amount ranging from 5 to 40 mole %. Within these ranges though, the level of the acetylacetonate compound is empirical.

In the preparation of nitrobenzene the reaction is maintained at a temperature sufficient to effect a reaction involving $N_2O_4$ and the aromatic hydrocarbon to yield a nitrosubstituted compound. The temperature is preferably above about $-11°$ C., the melting point of nitrogen tetroxide, to about 21° C., the boiling point of nitrogen tetroxide, when operating at atmospheric pressure. However, temperatures above and below 21° C. may be used with a reaction medium comprising an inert organic co-solvent saturated with gaseous $N_2O_4$.

Above 21° C., the vapor pressure of nitrogen tetroxide is greater than one atmosphere, attaining a value of about five atmospheres at 60° C. and twenty atmospheres at about 100° C. Accordingly, temperatures above 21° C. may also be used provided the reaction pressure is sufficient to maintain the nitrogen tetroxide in the liquid reaction medium. (As a word of caution, the pressurized reactions above 21° C. present the potential for runaway oxidation and detonation!) Preferably the pressure utilized for carrying out the reaction is that autogenous pressure which is sufficient to maintain the nitrogen tetroxide in essentially liquid phase at the reaction temperature. When utilizing these temperatures and pressures, the reaction is allowed to proceed until a desired conversion is obtained or the reaction is complete. Normally, the reaction is carried out within about 1.5 to 3 hours.

Although the reaction of the benzene will typically be performed in the presence of a great excess of nitrogen tetroxide and substantially selectively affords the moninitro product, it is nevertheless possible to further control the reaction to selectively produce the mononitroaromatic hydrocarbon. This can be achieved by controlling the reaction time and ceasing the reaction before greater than minor quantities of the dinitroaromatic compounds are produced.

After initial product formation occurs, the resultant product is stable in the reaction medium. Prolonged reaction times would not result in product degradation, only in the production of dinitrosubstituted product.

Recovery of the nitro compound from the reaction mixture can be accomplished by conventional techniques, these techniques generally involving a distillation. Illustratively, the liquid nitrogen tetroxide can be allowed to distill from the reaction vessel and the residue can be subjected to a distillation process to yield the desired product.

In general, the nitration process comprises introducing liquid nitrogen tetroxide into a temperature controlled reaction vessel. It is also possible to directly condense nitrogen tetroxide in the reaction vessel. An inert organic co-solvent is added to the reaction vessel before or after the introduction of the nitrogen tetroxide.

Oxygen is admitted into the liquid nitrogen tetroxide through a feed tube below the surface until any trace of nitrogen trioxide, which is green in color, has been oxidized to nitrogen tetroxide. When this operation is completed and a straw colored liquid which is characteristic of nitrogen tetroxide remains, the oxygen flow is terminated. Nitrogen gas is then bubbled through the reaction mixture to purge excess oxygen from the system. The nitrogen purge of the reaction medium is optional but recommended since it is suspected that oxygen generates phenolic by-products. The metal acetylacetonate is carefully added to the liquid reaction medium followed by benzene although this order of addition may be reversed. If compatible, the metal and the benzene can be added as one.

It has also been discovered that the nitration proceeds at a faster rate if the benzene is added to the $N_2O_4$ reaction medium followed by the metal acetylacetonate (fast mode) in contrast to first adding the metal acetylacetonate followed by benzene addition (slow mode).

The metal acetylacetonate promoted nitration reaction may also be performed in a reaction medium comprising gaseous nitrogen tetroxide bubbling into an inert organic solvent, preferably saturating the organic solvent with the gaseous $N_2O_4$.

If the reaction is proceeding at atmospheric pressure and a temperature of 20° C. or less, a condenser above the reaction vessel is used to recondense any nitrogen tetroxide vapors. At superatmospheric pressures a pressure reaction vessel, which may be fitted with a reflux condenser to remove the heat of reaction, is employed.

The presence of an organic cosolvent is important for another reason. The powdered metal acetylacetonates usually dissolve safely when slowly dropped into a stirring quantity of nitrogen tetroxide. However, when nitrogen tetroxide is added to several milligrams of the solid metal compounds, a brilliant flame erupts. Needless to say, the former addition mode is recommended, and with care if a nitration is performed without an inert organic co-solvent.

The following examples illustrate the nature of the inventive process and are not intended to limit the scope of the invention.

EXAMPLE 1

For Runs 1-9 nitrogen tetroxide was condensed into a reaction flask cooled to 0° C. As an inert organic co-solvent nitromethane was added to the liquid nitrogen tetroxide for Runs 2-9. The green tinted, liquid nitrogen tetroxide reaction medium was oxidized to a straw color by bubbling oxygen beneath the surface at about 10 scc/min to ensure that the small quantities of NO always present in the $N_2O_4$ are oxidized to $NO_2$. Flow of oxygen was stopped and nitrogen was bubbled through the reaction medium for at least two minutes to remove any dissolved oxygen.

Next, toluene (Runs 1-9) and a promoter (Runs 3-9) were added to the reaction medium maintained at 0° C. A small amount of nitrobenzene was also added as an internal standard. Samples were removed periodically and mixed with an equal volume of methylene chloride for gas chromatographic analysis.

Table 1 shows the quantities of reactants and co-solvent and the data for the products of the reaction.

TABLE 1

| Run | Promoter (mmole) | $N_2O_4$ ml | $CH_3NO_2$ ml | Toluene mmole | % Toluene Converted to MNT in (min) | Isomer Ratio o:m:p | % MNT with respect to Promoter |
|---|---|---|---|---|---|---|---|
| 1 | None | 20 | — | 60.1 | 0.9 (101) | 53:4:43 | — |
| 2 | None | 5 | 20 | 60.0 | 0.1 (109) | 62:5:34 | — |
| 3 | Acetic Anhydride (7.35) | 10 | 10 | 60.0 | 12.1 (66) | 59:2:39 | 99.1 |
| 4 | 2,4 Pentanedione (acetylacetone) (14.26) | 5 | 20 | 60.1 | 11.7 (104) | 61:4:35 | 49.5 |
| 5 | Ethyl Acetoacetate (11.99) | 5 | 20 | 60.1 | 10.2 (102) | 61:3:36 | 51.3 |
| 6 | Acetic Acid (14.38) | 5 | 20 | 60.1 | 0.1 (149) | 63:3:34 | 0.4 |
| 7 | Succinic* Anhydride (14.25) | 5 | 20 | 60.1 | 0.4 (108) | 69:7:24 | 1.8 |
| 8 | Diethyloxalate (14.31) | 5 | 20 | 60.2 | 0.4 (108) | 60:5:35 | 1.6 |
| 9 | Dimedone (7.84) | 5 | 20 | 60.1 | 0.3 (145) | 62:5:33 | 2.3 |

*Most of the anhydride remained undissolved.

Runs 1 and 2 were background runs using liquid $N_2O_4$ and liquid $N_2O_4$/nitromethane ($CH_3NO_2$) reaction media, respectively. These runs showed that less than 1% toluene was converted to a mononitrotoluene (MNT) in a little over 100 minutes.

The beta-dicarbonyl promoters acetic anhydride (Run 3), acetylacetone (Run 4) and ethyl acetoacetate (Run 5) showed substantial production of mononitrotoluene after about 100 minutes, i.e. at least about 50% mononitrotoluene production with respect to molar quantity of promoter. Acetic anhydride afforded nearly an equimolar amount of mononitrotoluenes. Acetic acid (Run 6), on the other hand, gave only 0.4% mononitrotoluenes.

Succinic anhydride (Run 7) and dimedone (Run 9), which are beta-dicarbonyl compounds that are not structurally orientable as a "W" having a carbonyl group at each apex, gave only about 0.4% toluene conversion to mononitrotoluene and about 2% mononitrotoluene with respect to promoter.

Diethyloxalate (Run 8), which is an example of an alpha-dicarbonyl compound, gave results comparable to succinic anhydride and dimedone.

EXAMPLE 2

For Run 10 nitrogen tetroxide (20 ml) was condensed into a reaction flask cooled to 0° C. The green tinted nitrogen tetroxide liquid was oxidized to a rich straw color by bubbling oxygen beneath the surface at a rate of 10 scc/min. Flow of oxygen was stopped and nitrogen was bubbled through the solution for two minutes to remove any dissolved oxygen.

Next, 2.79 mmoles of cobalt(III)acetylacetonate were introduced into the reaction vessel. The green solid immediately dissolved in the liquid and a dark red solution was obtained. To the solution was then added 11.26 mmoles of benzene, together with 5.0 mmoles of 4-nitrotoluene as an internal standard for later gas chromatographic analysis. The reaction was maintained at about 0° C. Samples were removed periodically and mixed with an equal volume of methylene chloride for gas chromatographic analysis.

TABLE 2

RUN 10

| SAMPLE | Time min. | NB mmoles | DNB mmoles | NB:DNB | % yield NB With respect to benzene | % yield NB With respect to Co(acac)₃ |
|---|---|---|---|---|---|---|
| A | 20 | 0.30 | .02 | 15.0 | 2.7 | 10.8 |
| B | 59 | 0.86 | .02 | 43.0 | 7.6 | 30.8 |
| C | 98 | 1.71 | .04 | 42.8 | 15.2 | 61.3 |
| D | 130 | 2.32 | .06 | 38.7 | 20.6 | 83.2 |
| E | 183 | 2.89 | .09 | 32.1 | 25.7 | 103.6 |
| F[a] | 291 | 3.36 | .11[b] | 30.5 | 29.8 | 120.4 |

[a]Phenols <0.04 mmoles
[b]o:m:p = 6:67:27

Table 2 presents the gas chromatography yield data for samples A–F of Run 10 which were taken at various times during the course of the nitration reaction. The quantities (mmoles) of nitrobenzene (NB) and dinitrobenzenes (DNB) are set forth. The percent yield of nitrobenzene with respect to the limiting starting quantity of cobalt(III)acetylacetonate appeared to be approaching a limit after 291 minutes of reaction time. While samples A–F showed a steady increase in nitrobenzene and dinitrobenzenes content, the nitrobenzene:dinitrobenzenes ratio steadily decreased with time, not considering the first sample. Nevertheless, it is readily apparent from the data that the nitration reaction selectively afforded primarily the mononitro substituted product.

EXAMPLE 3

The procedure of Example 2 was followed for Run 11 using 40 ml N₂O₄ liquid; 5.41 mmoles cobalt(III)acetylacetonate; 150 mmoles benzene; 5 mmoles 4-nitrotoluene internal standard.

TABLE 3

RUN 11

| SAMPLE | Time min. | NB mmoles | DNB mmoles | NB:DNB | % yield NB With respect to benzene | % yield NB With respect to Co(acac)₃ |
|---|---|---|---|---|---|---|
| A | 10 | 2.95 | 0.00 | — | 2.0 | 54.5 |
| B | 87 | 5.64 | 0.02 | 282.0 | 3.8 | 104.3 |
| C | 130 | 6.93 | 0.08 | 86.6 | 4.6 | 128.1 |
| D[a] | 207 | 7.34 | 0.09[b] | 81.6 | 4.9 | 135.7 |

[a]Phenols <0.04 mmoles.
[b]The final product had a dinitrobenzene ratio of o:m:p = tr:81:19.

Table 3 shows the quantities of nitrobenzene and dinitrobenzenes in the various samples taken during the course of the reaction. It appears from the data that after about 2 hours of reaction time, the reaction was approaching its limit based on the limiting quantity of transition metal beta-dicarbonyl compound in the reaction medium. Once again, it can be seen that the nitration process is substantially selective to mononitrobenzene, especially at short reaction times. At longer reaction times the dinitrobenzenes content increases, but the nitrobenzene:dinitrobenzenes ratio is still very high.

EXAMPLE 4

The procedure of Example 2 was followed for Run 12 using as starting materials 17 ml N₂O₄ liquid; 2.84 mmoles cobalt(III)acetylacetonate; 37.63 mmoles toluene; 5 mmoles nitrobenzene internal standard.

TABLE 4

RUN 12

| SAMPLE | Time min. | MNT mmoles | MNT o:m:p | DNT mmoles | % yield MNT With respect to toluene | % yield MNT With respect to Co(acac)₃ |
|---|---|---|---|---|---|---|
| A | 15 | 1.20 | 49:3:48 | — | 3.2 | 42.3 |
| B | 86 | 3.98 | 50:2:49 | — | 10.6 | 140.1 |
| C | 135 | 4.20 | 51:1:48 | — | 11.2 | 147.9 |
| D | 205 | 5.15 | 51:2:47 | — | 13.7 | 181.3 |
| E[a] | 205 | 4.34 | 56:2:43 | 0.0366[b] | 11.5 | 154.2 |

[a]Sample E is Sample D washed with 5% NaOH.
[b]The final base washed product had the following DNT's ratio: 2,6 DNT:2,5 DNT:(2,3 DNT + 2,4 DNT):3,5 DNT:3,4 DNT = 4:11:31:35:19 with MNT's:DNT's = 119

As can be seen in Table 4 the nitration reaction was for the most part substantially completed after about 86 minutes. The reaction was faster than those for benzene and again provided product yields that exceeded the starting quantity of cobalt(III)acetylacetonate. The nitration reaction readily afforded mononitrotoluenes (MNT) without the production of any substantial quantities of dinitrotoluenes (DNT). The nitration reaction shows that the nitration rate increased appreciably after the flow of oxygen was initiated.

TABLE 5

RUN 13

| SAMPLE | Time min. | NB mmoles | DNB mmoles | NB:DNB | % yield NB With respect to benzene | With respect to Co(acac)$_3$ |
|---|---|---|---|---|---|---|
| A | 20 | 0.14 | 0.001 | 140.0 | 1.3 | 5.7 |
| B | 59 | 0.33 | 0.004 | 82.5 | 3.0 | 13.5 |
| C | 130 | 0.64 | 0.010 | 64.0 | 5.7 | 26.1 |
| D | 183 | 0.86 | 0.013 | 66.2 | 7.7 | 35.1 |
| E | 291 | 1.13 | 0.025$^a$ | 45.2 | 10.1 | 46.1 |
| *F | 353 | 3.45 | 0.130 | 26.5 | 31.0 | 140.8 |
| G | 380 | 4.37 | 0.170 | 25.7 | 39.2 | 178.4 |
| H | 431 | 5.52 | 0.198$^b$ | 27.9 | 49.5 | 225.3 |

$^a$o:m:p = 7:64:29
$^b$o:m:p = 6:65:29
*Subsurface oxygen flow commenced primarily affords mononitrotoluene having ortho or para nitrosubstitution.

Cobalt(III)acetylacetonate was present in Examples 2-4 in limiting quantities. Without wishing to be bound by any particular theory, it appears that the initially rapid nitrations slowed, presumably, as the cobalt(III) cation was consumed in the process, i.e. reduced to cobalt(II).

Advantageously, a useful nitration system would include a step or steps in which the transition metal cation in its lower oxidation state were reoxidized. A desirable system would be one in which nitration takes place in the absence of oxygen, with the metal cation restored to its original oxidation state in a separate stage, such as an external oxidation loop. Appropriate oxidation procedures would include the use of oxygen gas or electrochemical oxidation.

It should also be pointed out that the yield of nitrated product based on the added transition metal acetylacetonate was greater than 100% in Examples 2-4 because acetylacetonate is enhancing the nitration reaction in some unknown manner.

EXAMPLE 5

The procedure of Example 2 was followed for Run 13 using 20 ml N$_2$O$_4$ liquid; 2.45 mmole cobalt(III)acetylacetonate; 11.14 mmole benzene and 0.82 mmoles 4-nitrotoluene. A nitrogen purge at about 10 scc/min was continued through the first 291 min at which time the nitrogen flow was ceased and a subsurface flow of oxygen at about 20 scc/min was initiated and continued through the remainder of the reaction. Table 5 shows the data for samples A-H which were taken at the designated times during the nitration reaction. The data Without being held to any particular theory or explanation, it is believed that this Example indicates that oxygen passed through the nitration reaction medium apparently oxidizes the "spent" transition metal cation, Co(II), to its higher oxidation state, Co(III), whereupon it could again catalyze the nitration of the aromatic compound along with the acetylacetonate groups.

This Example also suggests that the nitration process may be promoted by the combination of a small amount of a transition metal cation in its higher oxidation state and the presence of oxygen to constantly reoxidize the "spent" transition metal cation from its reduced form $M^{+(n-1)}$ to the effective higher oxidation state $M^{+n}$, in the case where the oxidation states of the transition metal are separated by one unit.

EXAMPLE 6

Nitrogen tetroxide (20 ml) was condensed into a reaction flask cooled to 0° C. The green tinted nitrogen tetroxide liquid was oxidized to a rich straw color by bubbling oxygen beneath the surface. The flow of oxygen was stopped and nitrogen was bubbled through the solution for 25 minutes in Run 14 and for the duration of the run in Runs 15-18 to remove any dissolved oxygen.

Benzene was added to the liquid nitrogen tetroxide together with a small amount (1-2 mmoles) 4-nitrotoluene as an internal standard for later gas chromatographic analysis. To this solution was added the metal acetylacetonate [M(acac)]. The reaction was maintained at about 0° C. Samples were removed periodically and mixed with an equal volume of methylene chloride for gas chromatographic analysis.

Table 6 shows the amount of benzene and metal acetylacetonate used in each example and the resultant data.

TABLE 6

| Run | M(acac) mmoles | Benzene mmoles | Sample time (min) | NB mmoles | DNB mmoles | NB:DNB | % Yield NB with respect to benzene | with respect to M(acac) |
|---|---|---|---|---|---|---|---|---|
| 14 | Fe(acac)$_3$ 1.85 | 19.8 | 30 | 1.13 | <0.05 | — | 5.7 | 51.1 |
|  |  |  | 70 | 3.20 | <0.05 | — | 16.2 | 173.0 |
| 15 | Co(acac)$_3$ 1.98 | 19.8 | 8 | 0.23 | 0.0008 | 298.1 | 1.2 | 11.6 |
|  |  |  | 38 | 2.47 | 0.08 | 31.7 | 12.9 | 128.8 |
|  |  |  | 68 | 3.1 | 0.14 | 22.1 | 16.4 | 163.6 |
| 16 | Mn(acac)$_3$* >2.0 | 17.54 | 7 | 0.48 | 0.007 | 58.3 | 2.8 | — |
|  |  |  | 58 | 1.16 | 0.025 | 46.4 | 6.8 | — |
|  |  |  | 98 | 2.27 | 0.16 | 12.6 | 14.4 | — |
| 17 | Cu(acac)$_2$* >3.8 | 17.49 | 13 | 0.44 | 0.0 | — | 2.5 | — |
|  |  |  | 55 | 1.20 | 0.017 | 70.6 | 7.0 | — |
|  |  |  | 116 | 2.35 | 0.11 | 21.4 | 14.3 | — |
| 18 | Ce(acac)$_4$ | 17.44 | 7 | 0.19 | 0.0 | — | 1.1 | 12.3 |

TABLE 6-continued

| | | | | | | % Yield NB | |
|---|---|---|---|---|---|---|---|
| Run | M(acac) mmoles | Benzene mmoles | Sample time (min) | NB mmoles | DNB mmoles | NB:DNB | with respect to benzene | with respect to M(acac) |
| | 1.54 | | 44 | 1.43 | 0.0 | — | 8.2 | 92.9 |
| | | | 91 | 1.64 | 0.024 | 68.3 | 9.5 | 108.1 |

*Part of the M(acac) ignited upon contact with $N_2O_4$ vapors.

Runs 14–18 show that acetylacetonate compounds of iron(III), cobalt(III), manganese(III), copper(II) and cerium(IV) promote the nitration of benzene in liquid $N_2O_4$ to yield substantially mononitrobenzene and only minor amounts of dinitrobenzenes.

EXAMPLE 7

The course of a reaction can often be significantly altered by solvents. Furthermore, solvents with very different dielectric constants may have different effects. With this in mind, the following runs were made to ascertain the effect, if any, of a co-solvent.

For Runs 19–24 of this example the procedure of Example 2 was followed using the reactants, co-solvents and quantities as set forth in Table 7. The metal acetylacetonate was added to the co-solvent and this mixture was added to the liquid $N_2O_4$.

TABLE 7

| RUN | $N_2O_4$(ml) | Co-Solvent (ml) | M(acac) (mmole) | Aromatic Cpd. (mmole) | % NB$^a$ with respect to metal (acac) |
|---|---|---|---|---|---|
| 19 | 20 | nitromethane 20 | Co(acac)$_3$ 15.99 | benzene 50 | 14 |
| 20 | 20 | nitromethane 14 | Fe(acac)$_3$ 10.04 | benzene 50 | 140 |
| 21 | 10$^b$ | nitromethane 20 | Li(acac) 2.44 | benzene 17.44 | 129.9 |
| 22 | 20 | nitromethane 30 | Co(acac)$_3$ 7.61 | benzene 50 | 33 |
| 23 | 20 | cyclohexane 30 | Co(acac)$_3$ 4.63 | benzene 50 | 77 |
| 24 | 20 | methylene chloride 20 | Co(acac)$_3$ 15.99 | benzene 50 | 14 |

$^a$No dinitrobenzenes (DNB) were detected. The DNB yield, if any, was estimated to be less than 0.1% of the molar quantity of starting metal (acac). No phenolics detected; estimated to be <0.4%
$^b$Plus 10 ml nitromethane.

As can be seen from Table 7, for the cobalt(III)acetylacetonate the use of a co-solvent, such as nitromethane in Example 22, cyclohexane in Example 23 and methylene chloride in Example 24, limited the conversion to about 33%, 77% and 14%, respectively. In contrast, the use of metal (acac) without an organic co-solvent in Example 2 provided high relative yields of nitroaromatic product, with the reaction rate falling off approximately after a stoichiometric quantity of product was formed.

The most favorable result was Run 20 using iron-(III)acetylacetonate/nitromethane which yielded mononitrobenzene (NB) at about 1.5 times the stoichiometric quantity of starting metal (acac) before being terminated.

The iron(III)acetylacetonae used in Run 20 was a free-flowing powder. However, when contacted by $NO_2$ fumes the material quickly agglomerates. If therefore cannot be added easily to the $N_2O_4$ medium without its first being dissolved in a co-solvent.

Significantly and unexpectedly, only occasional traces of phenolic products were observed in the Runs; on the basis of detection limits, the phenol:aromatic ratio was estimated to be less than 0.4%.

The second significant result is that the degree of dinitration in a reaction medium comprising a great excess of liquid $N_2O_4$ without a co-solvent is small. Most surprisingly, however, is that dinitration of benzene unexpectedly appears to be essentially eliminated with the addition of a co-solvent. Estimated detection limits suggest the dinitrobenzene:nitrobenzene ratio (Runs 19–24) to be less than 0.1% when an organic co-solvent is used.

STATEMENT OF INDUSTRIAL APPLICATION

The invention provides a method for the mononitration of benzene by a metal acetylacetonate in a nitrogen tetroxide/inert organic solvent reaction medium. Benzene is nitrated by the inventive process to nitrobenzene which is used commercially in the manufacture of aniline, a valuable starting material for the manufacture of dyes, medicinals, resins and varnishes.

We claim:

1. In a process for the nitration of an aromatic hydrocarbon, the method for mononitrating benzene which comprises reacting benzene with nitrogen tetroxide in an inert organic solvent containing an effective amount of a metal acetylacetonate at a temperature sufficient to effect nitration.

2. The invention of claim 1 wherein the metal acetylacetonate is an alkali metal or alkaline earth metal acetylacetonate.

3. The invention of claim 1 wherein the metal acetylacetonate is lithium acetylacetate.

4. The invention of claim 1 wherein the metal acetylacetonate is a transition metal acetylacetonate.

5. The invention of claim 4 wherein the transition metal acetylacetonate is an acetylacetonate of a first row transition metal of the Periodic Table.

6. The invention of claim 5 wherein the transition metal is titanium, vanadium, chromium, manganese, iron, cobalt, nickel or copper.

7. The invention of claim 1 wherein the nitration reaction is performed at a pressure sufficient to maintain the nitrogen tetroxide in the liquid state.

8. The invention of claim 1 or 7 wherein the reaction is maintained at a temperature from about −11° to 21° C. and atmospheric pressure.

9. The invention of claim 1 wherein the reaction is maintained at a temperature above about 21° C. and superatmospheric pressure.

10. The invention of claim 1 wherein the reaction medium comprises an inert organic solvent and liquid nitrogen tetroxide.

11. The invention of claims 1 or 10 wherein the organic solvent is a nitroaliphatic, nitroaromatic, acyclic aliphatic, cyclic aliphatic or halogenated aliphatic.

12. The invention of claim 11 wherein the organic co-solvent is nitromethane, cyclohexane or methylene chloride.

13. In a process for the nitration of an aromatic hydrocarbon, the method which comprises reacting benzene with liquid nitrogen tetroxide in an inert organic solvent containing an effective amount of a metal acetylacetonate at a temperature sufficient to effect nitration and a pressure sufficient to maintain the nitrogen tetroxide as a liquid.

14. The invention of claim 13 wherein the metal acetylacetonate is a transition metal acetylacetonate.

15. The invention of claim 4 or 14 wherein the nitration reaction is performed in the presence of oxygen.

16. The invention of claim 4 or 14 wherein the nitration reaction includes the step of reoxidizing the spent transition metal cation.

* * * * *